(12) United States Patent
Le Page et al.

(10) Patent No.: US 7,276,113 B2
(45) Date of Patent: Oct. 2, 2007

(54) SELF-EMULSIFYING PIGMENTS

(75) Inventors: Mark G. Le Page, Dudley, MA (US); William Zavadoski, Madison, CT (US); Shigeru Kishida, Storrs, CT (US); Yoshiaki Kawasaki, Woodstock, CT (US)

(73) Assignee: U.S. Cosmetics Corporation, Dayville, CT (US)

( * ) Notice: Subject to any disclaimer, the term of this patent is extended or adjusted under 35 U.S.C. 154(b) by 184 days.

(21) Appl. No.: 11/100,484

(22) Filed: Apr. 7, 2005

(65) Prior Publication Data

US 2006/0225616 A1  Oct. 12, 2006

(51) Int. Cl.
C08K 5/00 (2006.01)

(52) U.S. Cl. .............. 106/499; 106/31.65; 106/31.86; 106/287.16; 106/481

(58) Field of Classification Search ............. 106/499; 424/62, 63, 64, 65, 66, 67, 68
See application file for complete search history.

(56) References Cited

U.S. PATENT DOCUMENTS

| | | | | |
|---|---|---|---|---|
| 4,032,357 | A | 6/1977 | Rees et al. | 106/288 Q |
| 4,622,074 | A | 11/1986 | Miyoshi et al. | 106/308 F |
| 4,648,908 | A | 3/1987 | Takasuka et al. | 106/308 F |
| 5,143,722 | A * | 9/1992 | Hollenberg et al. | 424/63 |
| 5,387,624 | A * | 2/1995 | Morita et al. | 523/220 |
| 5,672,340 | A * | 9/1997 | Sun et al. | 424/66 |
| 5,922,121 | A * | 7/1999 | Kwan | 106/460 |
| 6,051,645 | A | 4/2000 | Suzuki et al. | 524/500 |
| 6,096,338 | A * | 8/2000 | Lacy et al. | 424/455 |
| 6,296,860 | B1 * | 10/2001 | Hasegawa et al. | 424/401 |
| 6,368,397 | B1 * | 4/2002 | Ichizawa et al. | 106/31.65 |
| 6,482,411 | B1 | 11/2002 | Ahuja et al. | |
| 6,709,662 | B1 * | 3/2004 | Gers-Barlag et al. | 424/401 |
| 2003/0196569 | A1 * | 10/2003 | Yatake et al. | 106/31.58 |

FOREIGN PATENT DOCUMENTS

| | | |
|---|---|---|
| EP | 0 596 465 A1 | 5/1994 |
| WO | 95/11943 | 5/1995 |

OTHER PUBLICATIONS

Hays, B.G., et al., Surface Treatment of Organic Pigments for Printing Ink Applications, American Inkmaker, MacNair-Dorland, New York, NY, US, vol. 62, No. 6, Jun. 1984, pp. 28-50.

* cited by examiner

*Primary Examiner*—David R. Sample
*Assistant Examiner*—Abraham M. Matthews
(74) *Attorney, Agent, or Firm*—Pillsbury Winthrop Shaw Pittman, LLP

(57) ABSTRACT

This invention relates to a surface-modified pigment having at least two surface-active agents chemically immobilized onto the surface of the pigment. The first surface-active agent has an HLB of about 10 or more, the second surface-active agent has an HLB of 9 or less, and the difference in HLB between the first and second surface-active agents is at least about 5. The surface-modified pigments are self emulsifying and are applicable for use in water-based cosmetic systems and toiletry products.

21 Claims, No Drawings

SELF-EMULSIFYING PIGMENTS

FIELD OF THE INVENTION

This invention relates to surface-treated pigments for cosmetic products such as foundations, lip sticks, lotions, and creams.

BACKGROUND OF THE INVENTION

In recent years, pigments have been improved to provide long lasting cosmetics with a smoother consistency. In obtaining these desirable traits, the focus has largely been on the hydrophobic properties of the surface treatments on the pigments, and improvements in the dispersibility of surface treated pigments into an oil phase. However, when pigments are used in cosmetic systems, such as foundations, lip sticks, lotions, or creams, the pigments must be dispersed in an aqueous phase for ease of removing the cosmetic pigments from the skin. To disperse the now-hydrophobic pigment in an aqueous phase, emulsifiers, often times many emulsifiers, are typically used. Without these emulsifiers, dispersion in water-based systems often becomes problematic. However, the use of emulsifiers also has its drawbacks, as emulsifiers tend to be irritating to the skin and eye mocosa, especially on individuals with sensitive conditions.

Accordingly, what is needed in the art is a pigment that can be used in cosmetic systems without using a significant amount of emulsifiers.

BRIEF SUMMARY OF THE INVENTION

This invention relates to a surface-modified pigment having at least two surface-active agents chemically immobilized onto the surface of the pigment, wherein the first surface-active agent has a hydrophilic-lipophilic balance of about 10 or more, the second surface-active agent has a hydrophilic-lipophilic balance of about 9 or less, and the difference in the hydrophilic-lipophilic balance values between the first and the second surface-active agent is at least about 5. The first surface-active agent contains at least one functional group selected from the group consisting of a carboxyl group, a phosphorous group, a sulfur group, and a silane group, and the second surface-active agent contains at least one functional group selected from the group consisting of a carboxyl group, a phosphorous group, and a silane group.

This invention also relates to a waterborne surface-modified pigment composition having less than 5 wt % surfactant in the composition.

This invention also relate to a process for making a surface-modified pigment, comprising the steps of: (a) providing a pigment, and (b) chemically immobilizing the surface of the pigment with at least two surface-active agents to produce a surface-modified pigment. The first surface-active agent has a hydrophilic-lipophilic balance of about 10 or higher, the second surface-active agent has a hydrophilic-lipophilic balance of about 9 or lower, and the difference in the hydrophilic-lipophilic values between the first and the second surface-active agents is at least about 5. The first surface-active agent contains at least one functional group selected from the group consisting of a carboxyl group, a phosphorous group, a sulfur group, and a silane group, and the second surface-active agent contains at least one functional group selected from the group consisting of a carboxyl group, a phosphorous group, and a silane group.

DETAILED DESCRIPTION OF THE INVENTION

This invention relates to a surface-modified pigment having at least two surface-active agents chemically immobilized onto the surface of the pigment. The first surface-active agent has a relatively high hydrophilic-lipophilic balance (HLB) and the second surface-active agent has a relatively low HLB. When used together, the pigment is imparted with the desired functionalities of both surface-active agents. The surface-active agent with the relatively low HLB imparts hydrophobic properties onto the surface of the pigment that help prevent the pigment from exhibiting the degradation properties associated with the pigment's inherently strong hydrophilic properties, such as fading and/or discoloration when contacted with perspiration. The surface-active agent with the relatively high HLB imparts hydrophilic properties onto the surface of the pigment so that the pigment can disperse in water-based cosmetic systems without the need for additional emulsifiers. Unlike conventional emulsifiers that are added after the pigment has been surface treated and are present only in the surface-treated pigment composition, these surface-active agents are chemically immobilized onto the surface of the pigment. The functionality of these surface-active agents, however, still acts in a manner sufficient to disperse the pigment in the water-based cosmetic systems. Therefore, there is no need for additional emulsifiers after the pigment has been treated because the surface-modified pigment, when modified with the two types of surface-active agents, is self emulsifying.

The term "pigment" as used herein includes pigments and pigment extenders. Any organic or inorganic pigment or pigment extender known in the art that is capable of being immobilized by surface-active agents may be used, although inorganic pigments are preferred. Acceptable pigments include, but are not limited to, titanium dioxide, zinc oxide, zirconium dioxide, iron oxides, ultramarine blues, mica, talc, chromium oxides, silica beads, nylon beads, magnesium silicate, aluminum silicate, fumed silica, starch, cotton powder, and beadyl beads.

The term "surface-active agent" encompasses all chemical agents known in the art that have the ability to affect the surface of a compound, including, but not limited to, surfactants, detergents, wetting agents, and emulsifiers.

The first surface-active agent having a relatively high HLB has an HLB of about 10 or higher. Preferably, the HLB is about 13 or higher, and most preferably the HLB of the first surface-active agent ranges from about 17 or higher.

The second surface-active agent having a relatively low HLB has an HLB of about 9 or lower. Preferably, the HLB is about 6 or lower, and most preferably the HLB of the second surface-active agent ranges from about 1 to about 4.

The difference is HLB values from the first surface-active agent to the second surface-active agent is at least about 5. Preferably, the difference in HLB is at least about 8, more preferably, at least about 11, and most preferably the difference in HLB ranges from about 13 to about 19.

The pigment may be modified with one or more first surface-active agents and one or more second surface-active agents. However, while more than one first surface-active agent and more than one second surface-active agent may be used, the HLB difference of 5 or more need only be satisfied for one first surface-active agent and one second surface-active agent. It may be desirable to add additional surface-active agents to the pigment to impart the pigment with the additional functionality of other surface-active agents. However, those additional surface-active agents would not necessarily qualify within the genera of first and second surface-active agents described herein.

The first surface-active agent preferably is a compound having one or more reactive groups, such as a carboxyl group, a phosphorous group, a sulfur group, or a silane group. The first surface-active agent should also preferably have one or more hydroxyl groups or alkylene oxide moieties, such as ethylene oxide or propylene oxide.

In a more preferred aspect of the invention, the first surface-active agent is a compound selected from the following structures, represented by Formulas I-VII:

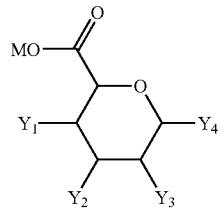

Formula I wherein $Y_1$, $Y_2$, $Y_3$, and $Y_4$ are independently selected from hydrogen, a hydroxyl group, an alkoxy group, or an oxo group, with the proviso that at least one of $Y_1$, $Y_2$, $Y_3$, and $Y_4$ is a hydroxyl group; and
M is either a hydrogen or a metal or its equivalent;

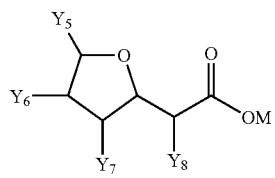

Formula II wherein $Y_5$, $Y_6$, $Y_7$, and $Y_8$ are independently selected from hydrogen, a hydroxyl group, an alkoxy group, or an oxo group, with the proviso that at least one of $Y_5$, $Y_6$, $Y_7$, and $Y_8$ is a hydroxyl group; and
M is either a hydrogen or a metal or its equivalent;

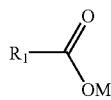

Formula III wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups; and
M is either a hydrogen or a metal or its equivalent;

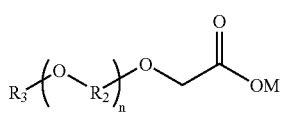

Formula IV wherein $R_2$ is ethylene, propylene, or butylene;
n is an integer from 1 to 60;
$R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and
M is either a hydrogen or a metal or its equivalent;

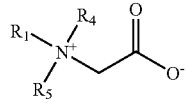

Formula V wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups; and
$R_4$ and $R_5$ are independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups;

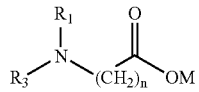

Formula VI wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups;
n is an integer from 1 to 60;
$R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and
M is either a hydrogen or a metal or its equivalent; and

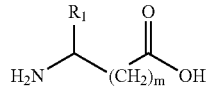

Formula VII wherein $R_1$ is a hydrogen, alkyl, alkyl amide, alkenyl, alkylnyl, alkoxy, aryl, cycloalkyl, or arylalkyl group, all of which may be substituted by one or more hydroxyl groups, and may further be substituted by one or more alkyoxyl, carboxyl, or oxo groups; and
m is an integer ranging from 0-2, meaning that when m=0, Formula VII represents an α-amino acid, when m=1, Formula VII represents a β-amino acid, and when m=2, Formula VII represents a γ-amino acid.

In instances when the substituent M is present in the compound, M represent either a hydrogen or a metal or its equivalent. When representing a hydrogen, a carboxyl group forms and is thus present on the compound; when representing a metal or its equivalent, the salt of a carboxyl group forms and is thus present in the compound. Of course, like any salt, the metal or its equivalent retains an overall positive charge and the oxygen retains an overall negative charge. Preferable metals include sodium, potassium, calcium, aluminum, and zinc, and preferable metal equivalents include amines such as monoethanolamine, diethanolamine, triethanolamine and ammonium, and organic bases such as lysine and arginine.

Except as provided below, the alkyl, alkyl amide, alkenyl, alkylnyl, and alkoxy, groups listed as possible substituents in the above formulas are preferably based upon alkyl groups having 1-24 carbon atoms, more preferably 1-6 carbon atoms; the aryl, cycloalkyl, and arylalkyl groups preferably contain 6-24 carbon atoms, more preferably 6-10 carbon atoms.

In Formula I, $Y_1$, $Y_2$, $Y_3$, and $Y_4$ are preferably all hydroxyl groups; in Formula II, $Y_5$ is preferably an oxo group, and $Y_6$, $Y_7$, and $Y_8$ are preferably all hydroxyl groups; in Formula III, $R_1$ is preferably an alkyl group, such as an ethyl, pentyl, hexyl, or heptadecyl ($C_{17}$) group substituted with 1-6 hydroxyl groups, or a benzyl group substituted with 1-3 hydroxyl groups; in Formula IV, $R_3$ is preferably an unsubstituted alkyl group or an alkyl group substituted with a carboxyl group; in Formula V, $R_4$ and $R_5$ are each preferably alkyl groups, such as methyl groups; in Formula VI, $R_1$ is preferably an alkyl group, such as an ethyl group, substituted with a hydroxyl group and n is preferably 1 or 3.

Most preferably, the first surface-active agents are lactates, gluconates, galacturonic acid, glucarolactone, gallic acid, glucoheptanoic acid, amino acids such as thereonine and serine, 12-hydroxystearic acid, laurylamidobetaine, stearyl amphoacetate, lauryl amphopropionate, stearyl amphopropionate.

The second surface-active agent preferably is compound having one or more reactive group, such as a carboxyl group, a phosphorous group, or a silane group, but having no hydroxyl groups or alkylene oxide moieties. The lack of hydroxyl groups and alkylene oxide moieties allows the second surface-active agent to retain a low HLB.

In a more preferred aspect of the invention, the second surface-active agent is selected from the following structures, represented by Formulas VIII-XII:

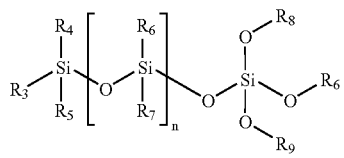

Formula VIII wherein $R_3$, $R_4$, $R_5$, $R_6$, $R_7$, $R_8$, and $R_9$ are each independently an alkyl, alkyl amide, alkenyl alkylnyl, alkoxy, aryl, cycloalkyl, or arylalkyl group, all of which may be substituted by one or more hydroxyl, alkyoxyl, carboxyl, or oxo groups; and
n is an integer from 1 to 60;

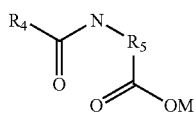

Formula IX wherein $R_4$ and $R_5$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and
M is either a hydrogen or a metal or its equivalent;

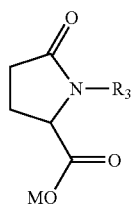

Formula X wherein $R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and
M is either a hydrogen or a metal or its equivalent;

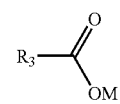

Formula XI wherein $R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups;
M is either a hydrogen or a metal or its equivalent; and

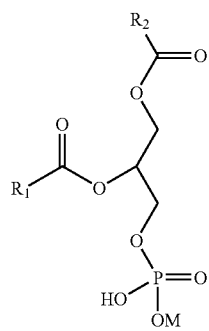

Formula XII wherein $R_1$ and $R_2$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and
M is either a hydrogen or a metal or its equivalent.

Except as provided below, the alkyl, alkyl amide, alkenyl, alkylnyl, and alkoxy groups listed as possible substituents in the above formulas are preferably based upon alkyl groups having 1-24 carbon atoms, more preferably 1-6 carbon atoms; the aryl, cycloalkyl, and arylalkyl groups preferably contain 6-24 carbon atoms, more preferably 6-10 carbon atoms.

In Formula VIII, $R_3$-$R_9$ are each preferably alkyl groups, such as methyl or ethyl groups; in Formula IX, $R_4$ is preferably an alkyl group, such as a tridecyl ($C_{13}$) group and $R_5$ is preferably an alkyl group, such as an propyl group, substituted by a carboxyl group; in Formula X, $R_3$ is preferably an alkyl group, such as a dodecyl group; and in Formula XI, $R_3$ is preferably an alkyl group, such as a tridecyl ($C_{13}$) group.

Most preferably, the second surface-active agents are N-myristoyl-L-glutamates, myristates, acyl amino acids such as acylglutamates, acylsarcosinates, acylglycinates, and acylalaninates, fatty acids and their salts, and glycerol phosphate esters such as lecithin.

Each surface-active agent should be present in an amount sufficient to impart the desired functionality onto the surface of the pigment. If it is desired that the pigment contain strong hydrophilic properties, then more of the first surface-active agent may be used in relation to the second surface-active agent; if it is desired that the pigment contain strong hydrophilic properties, then more of the first surface-active agent may be used in relation to the second surface-active agent.

The ratio between the first surface-active agent and the second surface-active agent may range from about 1:10 to about 10:1 by weight. Preferably the ratio ranges from about 1:4 to about 4:1 by weight.

The surface-modified pigments may contain conventional emulsifiers, suspending agents, emulsion stabilizers, or other agents known in the art.

The surface-active agents are chemically immobilized onto the surface of the pigment by the methods known in the art, such as those described in U.S. Pat. No. 5,897,868, herein incorporated by reference in its entirety. Chemical immobilization differs from adding the surface active agents to the pigment in that the treated pigment has a uniformly chemically bound reaction product. The reaction may be created by a water soluble compound having a lipophilic or hydrophilic moiety being absorbed onto the surface of the pigment. With the addition of, e.g., a water soluble salt of a polyvalent metal, a chemical bonding can be produced. The reaction product provides a chemical immobilized treatment onto the surface of the particles of the pigment or extender pigment. In contrast, the simple coating of a surface active agent renders it a free-flowing, unreliable, and inadequate functional layer in which is only absorbed onto the surface of the pigment.

Water-based pigment compositions, such as those useful for cosmetic and toiletry products, often have high levels of surfactants or surface-active agents, typically making up 20 wt % of the composition or more. The waterborne surface-modified pigment compositions of this invention, however, have less than 5 wt % surface-active agents in the composition, preferably less than 3 wt % surface-active agents. High levels of surface-active agents are not needed because, as described above, the surface-active agents become chemically immobilized in the pigment, thus allowing the pigment to be self-emulsifying.

The surface-modified pigment may be made by a process of (a) providing a pigment, and (b) chemically immobilizing the surface of the pigment with at least two surface-active agents, to produce a surface-modified pigment. The first surface-active agent has an HLB of about 10 or more, the second surface-active agent has an HLB of 9 or less, and the difference in HLB between the first and second surface-active agents is at least about 5. Preferred surface-active agents are those listed above.

A composition may be prepared in accordance with the following procedure although other methods are also suitable. Typically, the pigments or extender pigments being treated are mixed with 50 to 100% (based on weight of pigment and extender pigment) of water and dispersed. An aqueous solution of the second surface-active agent, such as a water-soluble alkali metal salt of a fatty acid, is added to the slurry and dispersed. Then 1 to 2 chemical equivalents of a water soluble salt of a polyvalent metal, such as an alkaline earth metal, aluminum, titanium, zinc, stannic, or zirconium sulfate or the like is added. The polyvalent metal will link the lipophilic moiety in the second surface-active agent to the surface of the particles of pigment or extender pigment. Next, the first surface-active agent, such as a water-soluble alkali metal salt of a sugar acid, is added to the slurry and dispersed. Then 1 to 2 chemical equivalents of a water soluble salt of a polyvalent metal, such as an alkaline earth metal, aluminum, titanium, zinc or zirconium sulfate or the like is added. The polyvalent metal will link the hydrophilic moiety in the first surface-active agent to the surface of the particles of pigment or extender pigment. The resultant surface-modified powder in having both lipophilic and hydrophilic properties from the first and second surface-active agents are dehydrated using a filter press and rinsed with purified water to remove any secondary salts, if desired. The filter cake is then baked in an oven for two hours past the point where the cake reaches a temperature of 100° C. After the filter cake has cooled, the cake is then crushed in an atomizer to produce a workable powder.

Alternatively, the first surface-active agent may be added to the pigment before the second surface-active agent. If desired, additional surface-active agents may also be added.

The product, now with a controlled HLB value, can be added to a water-and-oil mixture in a mixing state to produce a stable emulsion without additional emulsifiers.

The emulsion, when applied to the skin provides excellent skin adhesion, extended wear, and improved moisture-holding ability. Accordingly, the surface-modified pigments may be used in cosmetic products, such as foundations, lip sticks, eye shadow, lotions, creams, concealer, blush, eyeliners, mascara, eyebrow liner, lipliner, and sunscreen. It may also be used in toiletry products, such as deodorants, antiperspirants, and shower gels. When the surface-modified pigment is used in a cosmetic product or a toiletry product, other typical components used in making the cosmetic product or toiletry product can be added to the surface-modified pigment. For instance, lip stick will often contain various oils and waxes in addition to the pigments. As with any commercial product containing a pigment, the cosmetic and toiletry products may contain a single pigment or more than one pigment to obtain a particular color. The surface-modified pigments, or self-emulsifying pigments, may be used with other surface-modified pigments or with pigments that do not self emulsify.

The following examples are intended to illustrate the invention. These examples should not be used to limit the scope of the invention, which is defined by the claims.

EXAMPLE 1

Self-Emulsifying Titanium Dioxide Pigment

One hundred grams of titanium dioxide was added to 400 ml of water and mixed using a home mixer until well dispersed. Four grams of calcium myristate having an HLB value of 1 was dissolved in 50 ml of water heated at 60° C. then added to the above mixture and mixed for 10 minutes. While this was being stirred, 2 chemical equivalents of aluminum chloride aqueous solution, with respect of calcium myristate, was added dropwise. Four grams of ammonium lactate having an HLB value of 20 was dissolved in 50 ml of water heated at 50° C. then added to the above mixture and mixed for 10 minutes. While this was being stirred, 2 chemical equivalents of zinc sulfate aqueous solution, with respect to ammonium lactate, was added dropwise. The product was filtered using a Buchner funnel, followed by rinsing with purified water. The filter cake was then baked in an oven at a temperature of 100° C. for 2 hours to further dehydrate the filter cake. The filter cake was crushed and further pulverized to a more workable powder after cooling. This resulted in a titanium dioxide pigment chemically immobilized with aluminum di-myristate and zinc lactate.

EXAMPLE 2

Composition Containing Self-Emulsifying Titanium Dioxide

A mixture of 30 grams of isononyl isononanoate and 65 grams of water was blended using a lightning mixer for 2 minutes. Five grams of the chemically immobilized titanium dioxide from Example 1 was slowly added to the mixture to form an emulsion.

COMPARATIVE EXAMPLE 1

A mixture of 30 grams of isononyl isononanoate and 65 grams of water was blended using a lightning mixer for 2 minutes. Five grams of untreated titanium dioxide was slowly added to the mixture. The mixture separated in 10 minutes as no emulsion was formed.

EXAMPLE 3

Self-Emulsifying Red Iron Oxide Pigment

One hundred grams of red iron oxide pigment was added to 500 ml of water and mixed using a home type mixer until well dispersed. Four grams of sodium N-myristoyl-L-glutamate having an HLB value of 4 was dissolved in 50 ml of water heated at 60° C. then added to the above mixture and mixed for 10 minutes. While this was being stirred, 2 chemical equivalents of aluminum chloride aqueous solution, based on the sodium N-myristoyl-L-glutamate, was added dropwise. Four grams of potassium lactate having an HLB value of 17 was dissolved in 50 ml of water heated at 50° C. then added to the above mixture and mixed for 10 minutes. While this was being stirred, 2 chemical equivalents of zinc sulfate aqueous solution, based on the potassium lactate, was added dropwise. The product was filtered with suction using a Buchner funnel, followed by rinsing with purified water. The filter cake was then baked in an oven for two hours after the filter cake reaches a temperature of 100° C. to further dehydrate the filter cake. The cake was crushed and pulverized to a powder after cooling. This resulted in a red iron oxide pigment chemically immobilized with aluminum N-myristoyl-L-glutamate and zinc lactate.

EXAMPLE 4

Composition Containing Self-Emulsifying Red Iron Oxide Pigment

A mixture of 30 grams cyclomethicone, a cosmetic siloxane, and 65 grams of water was blended by a lightning mixer for 2 minutes. Five grams of the chemically immobilized red iron oxide pigment from Example 3 was slowly added to the mixture to form an emulsion.

EXAMPLE 5

Self-Emulsifying Mica Pigment

One hundred grams of mica pigment was added to 450 ml of water and mixed using a home type mixer until well dispersed. Three grams of hydrogenated egg yolk lecithin (phospholipids 30%, neutral fat 70%) having an HLB value of 2 was dissolved in 100 ml of water heated at 95° C. then added to the above mixture and mixed for 10 minutes. While this was being stirred, 2 chemical equivalents of aluminum sulfate aqueous solution, based on the phospholipids, was added dropwise. Four grams of potassium gluconate having an HLB value of 20 was dissolved in 50 ml of water heated to 50° C. then added to the above mixture and mixed for 10 minutes. While this was being stirred, 2 chemical equivalents of zinc sulfate aqueous solution, based on the potassium gluconate, was added dropwise. The product was filtered with suction using a Buchner funnel, followed by rinsing with purified water. The filter cake was then baked in an oven for 3 hours after the filter cake reached a temperature of 100° C. to further dehydrate the filter cake. The cake was crushed and pulverized to a powder after cooling. This resulted in a mica pigment chemically immobilized with lecithin and zinc gluconate.

EXAMPLE 6

Composition Containing Self-Emulsifying Mica Pigment

A mixture of 30 grams mineral oil and 65 grams of water was blended by a lightning mixer for 2 minutes. Five grams of the chemically immobilized mica pigment from Example 5 was slowly added to the mixture to form an emulsion.

COMPARATIVE EXAMPLE 2

One hundred grams of sericite was added to 450 ml of water and mixed using a home type mixer until well dispersed. Four grams of sodium N-myristoyl-L-glutamate having an HLB value of 4, was dissolved in 50 ml of water heated at 60° C. then added to the above mixture and mixed for 10 minutes. While this was being stirred, 2 chemical equivalents of aluminum chloride aqueous solution, based on the sodium N-myristoyl-L-glutamate, was added dropwise. Four grams of glycerin having an HLB value of 20 was dissolved in 50 ml of water heated at 50° C. then added to the above mixture and mixed for 10 minutes. The product was filtered with suction using a Buchner funnel, followed by rinsing with purified water. The filter cake was then baked in an over for two hours after the filter cake reached a temperature of 100° C. to further dehydrate the filter cake. The cake was crushed and pulverized to a powder after cooling. This resulted in sericite pigment chemically immobilized with aluminum N-myristoyl-L-glutamate; the glycerin did not chemically immobilize itself to the pigment, but instead was washed away.

The sericite pigment chemically immobilized with only one lipophilic surface-active agent only contains the lipophilic/oleophobic properties of that surface-active agent and therefore, when added to an oil/water mixture, will not form an emulsion unless emulsifiers are added.

COMPARATIVE EXAMPLE 3

One hundred grams of yellow iron oxide was added to 550 ml of water and mixed using a home type mixer until well dispersed. Two grams of calcium myristate was dissolved in 50 ml of water heated at 60° C. then added to the above mixture and mixed for 10 minutes. While this was being stirred, two chemical equivalents of aluminum chloride aqueous solution, with respect of calcium myristate, was added dropwise. The chemical result, aluminum di-myristate has an HLB of 1. Two grams of hydrogenated egg yolk lecithin (phospholipids 30%, neutral fat 70%) having an HLB value of 2 was dissolved in 100 ml of water heated at 95° C. then added to the above mixture and mixed for 10 minutes. While this was being stirred, 2 chemical equivalents of aluminum sulfate aqueous solution, based on the phospholipids, was added dropwise. The product was filtered using a Buchner funnel, followed by rinsing with purified water. The filter cake was then baked in an oven at a temperature of 100° C. for 2 hours to further dehydrate the filter cake. The filter cake was crushed and further pulverized to a more workable powder after cooling. This resulted in a yellow iron oxide pigment chemically immobilized with aluminum di-myristate and lecithin.

The yellow iron oxide pigment chemically immobilized with two lipophilic surface-active agents only contains the lipophilic/oleophobic properties of the surface-active agents. When added to an oil/water mixture the pigment did not form an emulsion. Only after the addition of emulsifiers was an emulsion formed with this pigment.

COMPARATIVE EXAMPLE 4

One hundred grams of black iron oxide was added to 400 ml of water and mixed using a home type mixer until well dispersed. Two grams of potassium lactate having an HLB value of 17 was dissolved in 50 ml of water and heated at 50° C. then added to the above mixture and mixed for 10 minutes. While this was being stirred, 2 chemical equivalents of zinc sulfate aqueous solution, based on the potassium lactate, was added dropwise. Two grams of potassium gluconate having an HLB value of 20 was dissolved in 50 ml of water heated at 50° C. then added to the above mixture and mixed for 10 minutes. While this was being stirred, 2 chemical equivalents aluminum sulfate aqueous solution, based on potassium gluconate, was added dropwise. The product was filtered using a Buchner funnel, followed by rinsing of purified water. The filter cake was then baked in an oven for three hours after the filter cake reached a temperature of 100° C. to further dehydrate the filter cake. The filter cake was crushed and further pulverized to a more workable powder after cooling. This resulted in black iron oxide pigment chemically immobilized coated with zinc lactate and aluminum gluconate.

The black iron oxide pigment chemically immobilized with two hydrophilic surface-active agents only contains the hydrophilic properties of the surface-active agents. When added to an oil/water mixture the pigment did not form an emulsion. Only after the addition of emulsifiers was an emulsion formed with this pigment.

EXAMPLE 7

Self-Emulsifying Yellow Iron Oxide Pigment

The procedure used in Example 3 was repeated except that 100 grams of yellow iron oxide pigment was used instead of the red iron oxide pigment. This resulted in a yellow iron oxide pigment chemically immobilized with aluminum N-myristoyl-L-glutamate and zinc lactate.

EXAMPLE 8

Self-Emulsifying Black Iron Oxide Pigment

The procedure used in Example 3 was repeated except that 100 grams of black iron oxide pigment was used instead of the red iron oxide pigment. This resulted in a black iron oxide pigment chemically immobilized with aluminum N-myristoyl-L-glutamate and zinc lactate.

EXAMPLE 9

Cosmetic Product

Two grams of Lipex L'Sens, a product containing soybean glycerides and shea butter produced by Karlshamns AB, was heated to 40° C. and added to 14 grams of Dermol 99, a product containing isononyl isononanoate produced by Alzo International Inc., 0.1 grams of Vitamin A palmitate, 0.1 grams of magnesium ascorbyl phosphate (C-Mate), and 0.5 grams of Vitamin E acetate. The composition was mixed together using a homogenizer. Sixty five grams of deionized water and 5 grams of butylene glycol were added and mixed for two minutes at room temperature. While mixing, the following pigments were added: 12.6 grams of the self-emulsifying titanium dioxide pigment of Example 1, 0.2 grams of the self-emulsifying red iron oxide pigment of Example 3, 0.4 grams of the self-emulsifying yellow iron oxide pigment of Example 7, and 0.1 grams of the self-emulsifying black iron oxide pigment of Example 8. While still mixing, the batch was heated to 50-60° C., and then cooled to room temperature.

A smooth, well-dispersed emulsion was formed with the self-emulsifying pigments holding the water and oil phases together. The resulting composition, which contains excellent moisturizing properties, is suitable for use in a variety of cosmetic applications.

What is claimed is:

1. A surface-modified pigment having at least two surface-active agents each of which is chemically immobilized onto the surface of the pigment, wherein
    the first surface-active agent has a hydrophilic-lipophilic balance of about 10 or higher and contains at least one functional group selected from the group consisting of a carboxyl group, the salt of a carboxyl group, a phosphorous group, a sulfur group, and a silane group;
    the second surface-active agent has a hydrophilic-lipophilic balance of about 9 or lower and contains at least one functional group selected from the group consisting of a carboxyl group, the salt of a carboxyl group, a phosphorous group, and a silane group; and
    the difference in the hydrophilic-lipophilic balance values between the first and the second surface-active agent is at least about 5.

2. The surface-modified pigment of claim 1, wherein the first surface-active agent has a hydrophilic-lipophilic balance ranging from about 14 to 18.

3. The surface-modified pigment of claim 1, wherein the first surface-active agent contains one or more hydroxyl groups or alkylene oxide moieties.

4. The surface-modified pigment of claim 3, wherein the alkylene oxide moieties are ethylene oxide moieties, propylene oxide moieties, or a combination thereof.

5. The surface-modified pigment of claim 3, wherein the first surface-active agent is a compound represented by any one of Formulas I-VII:

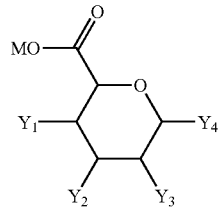

Formula I wherein $Y_1$, $Y_2$, $Y_3$, and $Y_4$ are independently selected from hydrogen, a hydroxyl group, an alkoxy group, or an oxo group, with the proviso that at least one of $Y_1$, $Y_2$, $Y_3$, and $Y_4$ is a hydroxyl group; and M is either a hydrogen or a metal or its equivalent;

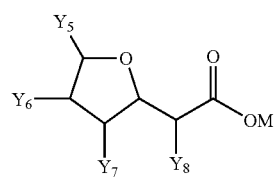

Formula II wherein $Y_5$, $Y_6$, $Y_7$, and $Y_8$ are independently selected from hydrogen, a hydroxyl group, an alkoxy group, or an oxo group, with the proviso that at least one of $Y_5$, $Y_6$, $Y_7$, and $Y_8$ is a hydroxyl group; and M is either a hydrogen or a metal or its equivalent;

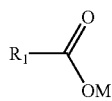

Formula III wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups; and M is either a hydrogen or a metal or its equivalent;

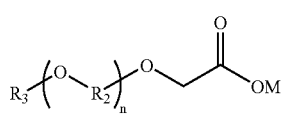

Formula IV wherein $R_2$ is ethylene, propylene, or butylene;

n is an integer from 1 to 60;

$R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent;

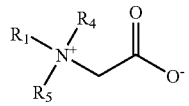

Formula V wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups; and $R_4$ and $R_5$ are independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and

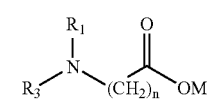

Formula VI wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups;

n is an integer from 1 to 60;

$R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent; and

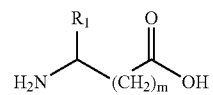

Formula VII wherein $R_1$ is a hydrogen, alkyl, alkyl amide, alkenyl, alkylnyl, alkoxy, aryl, cycloalkyl, or arylalkyl group, all of which may be substituted by one or more hydroxyl groups, and may further be substituted by one or more alkyoxyl, carboxyl, or oxo groups; and m is an integer ranging from 0-2.

6. The surface-modified pigment of claim 5, wherein the first surface-active agent is selected from the group consisting of lactates, gluconates, galacturonic acid, glucarolactone, gallic acid, glucoheptanoic acid, amino acids, 12-hydroxystearic acid, laurylamidobetaine, stearyl amphoacetate, lauryl amphopropionate, and stearyl amphopropionate.

7. The surface-modified pigment of claim 1, wherein the second surface-active agent has a hydrophilic-lipophilic balance ranging from about 1 to 4.

8. The surface-modified pigment of claim 1, wherein the second surface-active agent is devoid of hydroxyl groups and alkylene oxide moieties.

9. The surface-modified pigment of claim 8, wherein the surface-active agent is a compound represented by any one of Formulas VIII-XII

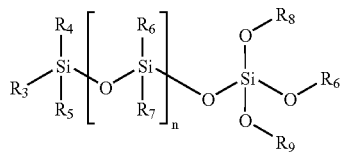

Formula VIII wherein $R_3$, $R_4$, $R_5$, $R_6$, $R_7$, $R_8$, and $R_9$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and n is an integer from 1 to 60;

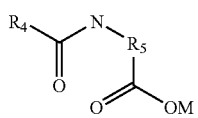

Formula IX wherein $R_4$ and $R_5$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent;

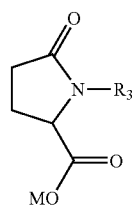

Formula X wherein $R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent;

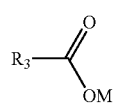

Formula XI wherein $R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent; and

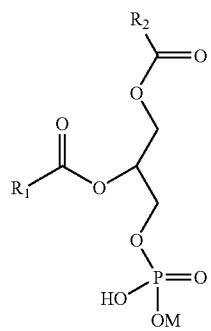

Formula XII wherein $R_1$ and $R_2$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent.

10. The surface-modified pigment of claim 9, wherein the second surface-active agent is selected from the group consisting of N-myristoyl-L-glutamates, myristates, acyl amino acids, fatty acids and their salts, and glycerol phosphate esters.

11. The surface-modified pigment of claim 1, further comprising emulsifiers, suspending agents, emulsion stabilizers, or a combination thereof.

12. A cosmetic comprising the surface-modified pigment of claim 1.

13. A toiletry product comprising the surface-modified pigment of claim 1.

14. A waterborne surface-modified pigment composition having at least two surface-active agents each of which is chemically immobilized onto the surface of the pigment, and having less than 5 wt % surface-active agents in the composition.

15. The waterborne surface-modified pigment composition of claim 14, having less than 3 wt % surface-active agents in the composition.

16. A process for making a surface-modified pigment, comprising the steps of:
   a. providing a pigment, and
   b. chemically immobilizing onto the surface of the pigment at least two surface-active agents, wherein
      i. the chemically immobilized first surface-active agent has a hydrophilic-lipophilic balance of about 10 or higher and contains at least one functional group selected from the group consisting of a carboxyl group, the salt of a carboxyl group, a phosphorous group, a sulfur group, and a silane group,
      ii. the chemically immobilized second surface-active agent has a hydrophilic-lipophilic balance of about 9 or lower and contains at least one functional group selected from the group consisting of a carboxyl group, the salt of a carboxyl group, a phosphorous group, and a silane group, and iii. the difference in the hydrophilic-lipophilic values between the first and the second chemically immobilized surface-active agents is at least about 5 to produce a surface-modified pigment.

17. The process of claim 16, wherein the first surface-active agent contains one or more hydroxyl groups or alkylene oxide moieties.

18. The process of claim 17 wherein the first surface-active agent is a compound represented by any one of Formulas I-VII:

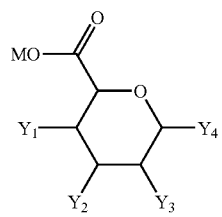

Formula I wherein $Y_1$, $Y_2$, $Y_3$, and $Y_4$ are independently selected from hydrogen, a hydroxyl group, an alkoxy group, or an oxo group, with the proviso that at least one of $Y_1$, $Y_2$, $Y_3$, and $Y_4$ is a hydroxyl group; and M is either a hydrogen or a metal or its equivalent;

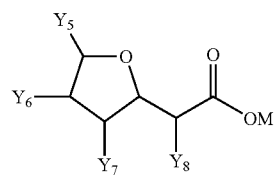

Formula II wherein $Y_5$, $Y_6$, $Y_7$, and $Y_8$ are independently selected from hydrogen, a hydroxyl group, an alkoxy group, or an oxo group, with the proviso that at least one of $Y_5$, $Y_6$, $Y_7$, and $Y_8$ is a hydroxyl group; and M is either a hydrogen or a metal or its equivalent;

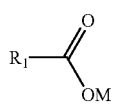

Formula III wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups; and M is either a hydrogen or a metal or its equivalent;

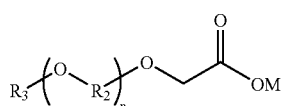

Formula IV wherein $R_2$ is ethylene, propylene, or butylene;

n is an integer from 1 to 60;

$R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent;

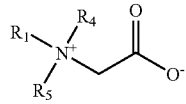

Formula V wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups; and $R_4$ and $R_5$ are independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups;

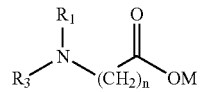

Formula VI wherein $R_1$ is an alkyl, alkyl amide, alkenyl, alkylnyl, alkoxy, aryl, cycloalkyl, or arylalkyl group, all of which are substituted by at least one hydroxyl group, and may further be substituted by one or more alkyoxyl, carboxyl, or oxo groups;

n is an integer from 1 to 60;

$R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent; and

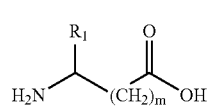

Formula VII wherein $R_1$ is a hydrogen, alkyl, alkyl amide, alkenyl, alkylnyl, alkoxy, aryl, cycloalkyl, or arylalkyl group, all of which may be substituted by one or more hydroxyl groups, and may further be substituted by one or more alkyoxyl, carboxyl, or oxo groups; and m is an integer ranging from 0-2.

19. The process of claim 16, wherein the second surface-active agent is devoid of hydroxyl groups and alkylene oxide moieties.

20. The process of claim 19, wherein the second surface-active agent is a compound represented by any one of Formulas VIII-XII:

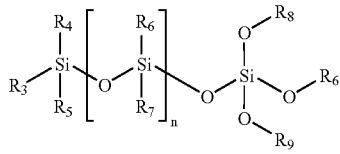

Formula VIII wherein $R_3$, $R_4$, $R_5$, $R_6$, $R_7$, $R_8$, and $R_9$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and n is an integer from 1 to 60;

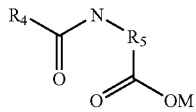

Formula IX wherein $R_4$ and $R_5$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent;

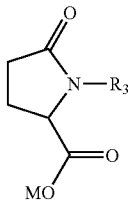

Formula X wherein $R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent;

Formula XI wherein $R_3$ is an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent; and

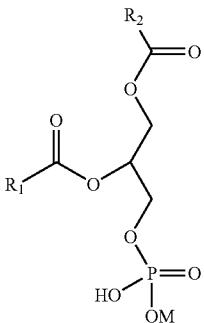

Formula XII wherein $R_1$ and $R_2$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and M is either a hydrogen or a metal or its equivalent.

21. The surface-modified pigment of claim 1, wherein the pigment is an inorganic pigment.

\* \* \* \* \*